US012599315B2

(12) United States Patent
Alessi et al.

(10) Patent No.: US 12,599,315 B2
(45) Date of Patent: Apr. 14, 2026

(54) WEARABLE AND PORTABLE SYSTEM AND METHOD FOR MEASURING CARDIAC PARAMETERS FOR DETECTING CARDIOPATHIES

(71) Applicant: STMICROELECTRONICS S.r.l., Agrate Brianza (IT)

(72) Inventors: Enrico Rosario Alessi, Catania (IT); Fabio Passaniti, Syracuse (IT); Oriana Rita Antonia Di Marco, Milan (IT)

(73) Assignee: STMICROELECTRONICS S.r.l., Agrate Brianza (IT)

( * ) Notice: Subject to any disclaimer, the term of this patent is extended or adjusted under 35 U.S.C. 154(b) by 280 days.

(21) Appl. No.: 18/456,227

(22) Filed: Aug. 25, 2023

(65) Prior Publication Data

US 2024/0074676 A1 Mar. 7, 2024

(30) Foreign Application Priority Data

Sep. 2, 2022 (IT) ........................ 102022000018060

(51) Int. Cl.
*A61B 5/11* (2006.01)
*A61B 5/00* (2006.01)
*A61B 5/349* (2021.01)

(52) U.S. Cl.
CPC ............ *A61B 5/1102* (2013.01); *A61B 5/349* (2021.01); *A61B 5/7239* (2013.01); *A61B 5/725* (2013.01); *A61B 2562/0219* (2013.01)

(58) Field of Classification Search
None
See application file for complete search history.

(56) References Cited

U.S. PATENT DOCUMENTS

2015/0065894 A1* 3/2015 Airaksinen .......... A61B 5/0002
702/19
2022/0125330 A1* 4/2022 Mac Quarrie ......... A61B 5/341

FOREIGN PATENT DOCUMENTS

WO WO 2019079829 A1 4/2019

OTHER PUBLICATIONS

Shafiq et al. Automatic Identification of Systolic Time Intervals in Seismocardiogram. Sci Rep. Nov. 22, 2016:6:37524. (Year: 2016).*
Cheng et al., "Study of the Correlation Between the Ratio of Diastolic to Systolic Durations and Echocardiography Measurements and Its Application to the Classification of Heart Failure Phenotypes," *International Journal of General Medicine* 14:5493-5503, 2021.

(Continued)

*Primary Examiner* — Ankit D Tejani
(74) *Attorney, Agent, or Firm* — Seed Intellectual Property Law Group LLP

(57) ABSTRACT

A system for measuring cardiac parameters uses a movements sensor to generate a seismocardiographic signal and a cardiac parameters calculation unit. The cardiac parameters calculation unit provides for generating an envelope signal correlated to the seismocardiographic signal; identifies, in the envelope signal, signal segments having a repetitive pattern; identifies, among the signal segments, pairs of successive peaks such that a first peak of each pair of successive peaks is a systolic peak and a second peak of each pair of successive peaks is a diastolic peak; and calculates a systolic period and a diastolic period for each pair of successive peaks.

13 Claims, 8 Drawing Sheets

(56)           References Cited

OTHER PUBLICATIONS

Jie et al., "Segmentation of Heart Sound Using Double-threshold," 2013 Fifth Conference on Measuring Technology and Mechatronics Automation, pp. 985-988. (5 pages).

Sharma et al., "A Novel Algorithm for HRV Estimation from Short-Term Acoustic Recordings at Neck," 2019 IEEE, pp. 6343-6346. (5 pages).

Sharma et al., "An Algorithm for Heart Rate Extraction From Acoustic Recordings at the Neck," *IEEE Transactions on Biomedical Engineering* 66(1):246-256, Jan. 2019. (12 pages).

Varghees et al,. "Automated PCG Signal Delineation Method for Heart Sound Analysis," 2014 IEEE. (7 pages).

Varghees et al., "Multistage decision-based heart sound delineation method for automated analysis of heart sounds and murmurs," *Healthcare Technology Letters* 2(6):156-163, 2015. (9 pages).

* cited by examiner

WEARABLE AND PORTABLE SYSTEM AND METHOD FOR MEASURING CARDIAC PARAMETERS FOR DETECTING CARDIOPATHIES

BACKGROUND

Technical Field

The present disclosure relates to a wearable and portable system and method for measuring cardiac parameters for detecting cardiopathies.

Description of the Related Art

In particular, the system may be associated with patches, adhesive electrodes, chest bands and the like, applicable to a person's sternum and is configured to provide data relating to a person's health state, for example through a mobile device such as a mobile phone, a smartwatch and the like.

Nowadays, more and more applications and programs are available, associable with dedicated devices or mobile devices, capable of allowing monitoring a person's health in normal living conditions and at any time of the day. These applications and programs are studied so as to be operative without having to be connected to complex and expensive machinery, and without requiring the presence of doctors and/or healthcare personnel.

In particular, these applications and programs aim to provide more and more health information in a way that is usable by individuals, with a good level of accuracy and seamlessly. Since they are associated with battery powered devices, it is desired that they have low power consumption.

In the case of cardiac activity monitoring, for example, there are already available programs and applications that are executable by portable devices and allow electrocardiograms (ECG) and photoplethysmography (PPG) to be performed. In particular, in the case of an electrocardiogram, analog devices and electrodes connected to the human body are used to detect biopotentials associated with heart pulses. In the case of photoplethysmography, optical elements, such as LEDs and photodiodes, allow the volumetric changes of the blood in the peripheral circulation to be monitored. In this manner, the heartbeat and its variability may be measured.

Recently, other heartbeat analysis techniques have emerged, but, in general, they require complex and expensive apparatuses and procedures and are therefore primarily suitable only for use in laboratories and medical practice settings. In fact, wearable and portable applications are very sensitive to disturbances that do not allow reliable results to be obtained.

For example, phonocardiograms (PCM), based on microphones, and echocardiograms, based on ultrasound, have been proposed. Recently, in a study, the relationship between phonocardiogram and blood pressure has been highlighted, in particular between the diastolic period based on PCM and Pulse Transit Time (PTT), in turn correlated with blood pressure.

Another technique recently proposed for studying the heartbeat consists in seismocardiography (SCG) which allows the chest vibrations associated with the heartbeat to be measured. For this purpose, the use of a highly sensitive accelerometer for detecting heart movements has already been proposed.

For example, "A Low Cost Sensing Device to Detect Cardiac Timing and Function," Anh Dinh et al., 2012 IEEE 18th International Mixed-Signal, Sensors, and Systems Test Workshop, 978-0-7695-4726-8/12 describes the relationship between ECG and SCG (see also FIGS. 1A and 1B attached, showing respectively an electrocardiographic plot and a corresponding seismocardiographic plot) and proposes the use of an accelerometer to detect the heart seismic movement, in association with an ECG sensor and a microphone, which measures the phonocardiogram. In particular, in this article, it is proposed to use the seismocardiographic signal to accurately measure mitral valve closure, aortic valve opening, ventricular expulsion, and so on. Furthermore, in this article it is stated that the seismocardiographic signal should allow a prediction of events based on the expected movements and the duration of the cardiac events, without however going into details on the necessary processings, but conversely indicating the need for further studies to determine the relationship between the timing of the SCG waveform and the cardiac timing.

Other documents (for example "Precision wearable accelerometer contact microphones for longitudinal monitoring of mechano-acoustic cardiopulmonary signals" by P. Gupta et al., npj Digital Medicine, https://www.nature.com/articles/s41746-020-0225-7, Feb. 12, 2020) describe the acquisition of the SCG signal through an accelerometer in combination with other sensors, or the use of the accelerometer in lieu of microphones to detect signal characteristics and compare them with standard values (see for example "Accelerometer Type Cardiac Transducer for Detection of Low-Level Heart Sounds, by V. Padmanabhan et al., IEEE TRANSACTIONS ON BIOMEDICAL ENGINEERING, VOL. 40, NO. 1, January 1993).

In "Automatic Identification of Systolic Time Intervals in Seismocardiogram," by G. Shafiq et al., https://doi.org/10.1038/srep37524 and in "Seismocardiographic adjustment of diastolic timed vibrations," by K. Tavakolian et al., DOI: 10.1109/EMBC.2012.6346794, the use of the SCG signal for the prediction of cardiac signal characteristics such as the duration of the systolic or diastolic period is discussed; however, these documents do not provide precise teachings for the implementation of devices and/or applications capable of processing such information in an automatic and usable manner by a portable and/or wearable device.

The solutions described do not allow providing portable and wearable devices capable of detecting cardiac parameters useful for the identification of cardiopathic situations at an early stage.

In fact, echocardiography is a non-portable and wearable medical instrument, and wearable and portable devices using a microphone for auscultation are sensitive to ambient acoustic noise which may hide or distort the results.

It has also recently been noted (see for example "Study of the Correlation Between the ratio of Diastolic to Systolic Durations and Echocardiography Measurement and Its Application to the Classification of Heart Failure Phenotypes" by L. Cheng et al., International Journal of General Medicine, 2021:14 5493-5503) that the ratio between the systolic period (S, hereinafter also referred to as S12) and the diastolic period (D, hereinafter also referred to as S21) is relevant as an index of cardiomyopathy and allows cardiac malfunctions to be detected at an early stage.

However, the use of the echocardiogram (as well as the phonocardiogram, which has been the subject of other studies and publications) is not suitable for portable devices.

BRIEF SUMMARY

Various embodiments of the present disclosure provide an alternative manner to obtain the systolic period (S), the diastolic period (D) and their ratio, such that it may be implemented in a portable/wearable device.

According to the present disclosure, a system and a method for detecting cardiac parameters are provided.

BRIEF DESCRIPTION OF THE SEVERAL VIEWS OF THE DRAWINGS

For a better understanding of the various embodiments of the present disclosure, embodiments thereof are now described, purely by way of non-limiting example, with reference to the attached drawings, wherein.

DETAILED DESCRIPTION

The present description refers to a system based on the technique called seismocardiography (SCG) which exploits accelerometers to measure the systolic and diastolic periods of the cardiac cycle.

Figures 1A, 1B, 2:
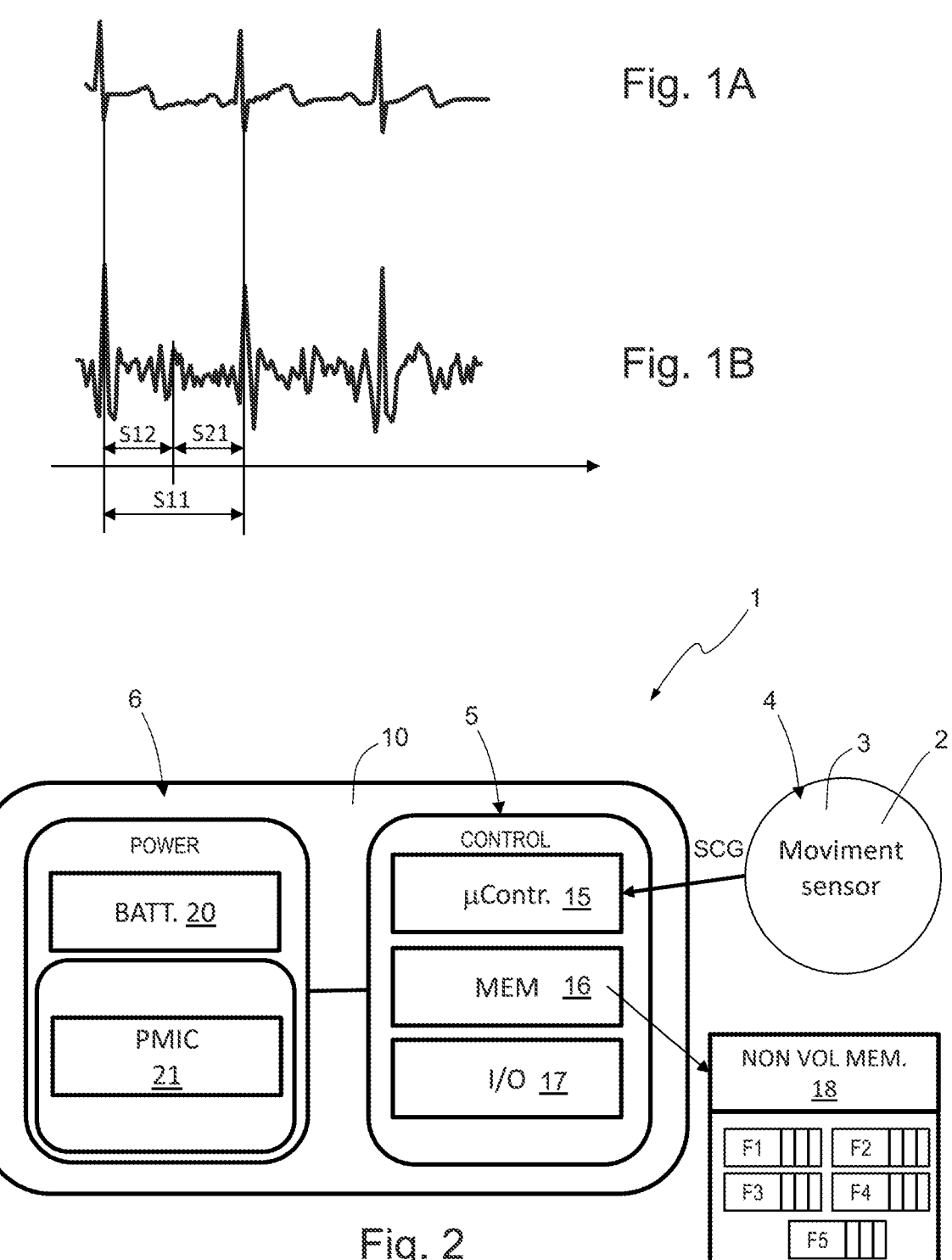
FIGS. 1A and 1B show an example of an electrocardiographic (ECG) plot and a corresponding seismocardiographic (SCG) signal acquired in a human patient.
FIG. 2 is a general block diagram of a cardiac parameters measuring system for detecting cardiopathies, according to an embodiment.

FIGS. 1A and 1B show an example of an electrocardiographic signal obtainable with portable apparatuses and a corresponding seismocardiographic signal detected by an accelerometer. In particular, the comparison of FIGS. 1A and 1B shows the correlation between the two signals and the possibility of detecting the cardiac period S11, the systolic period S12 and the diastolic period S21 through the seismocardiographic signal.

As explained above, these periods and in particular their ratio S12/S21 have been recognized as relevant for the calculation of the cardiomyopathy index, which in turn is important for the recognition of cardiopathies at an early stage.

FIG. 2 shows a system 1 for detecting cardiac parameters which allows the cardiac period S11, the systolic period S12 and the diastolic period S21 to be detected.

In detail, the system 1 of FIG. 2 comprises a detection part 4, a processing part 5 and a power supply part 6.

The detection part 4 here comprises a movement sensor 2. The movement sensor 2 is typically an accelerometer, integrated in a semiconductor chip and therefore having very reduced dimensions. The accelerometer may be for example a three-axis MEMS accelerometer or a six-axis IMU inertial platform, incorporating an accelerometer and a gyroscope.

The movement sensor 2 is associated, for example bonded or fixed, to a fixing element 3 which allows the positioning thereof on a patient's sternum and a good mechanical coupling, so as to be capable of detecting the heartbeat.

For example, the fixing element 3 may be a plaster, a suction cup element similar to the ECG detection electrodes, an elastic band and the like.

The movement sensor 2 generates a movement signal SCG sent to the processing part 5.

The movement sensor 2 may be connected to the processing part 5 by wire or by means of a wireless system; in this case it embodies a suitable interface (not shown), embodying known transmission circuits.

As an alternative to what has been shown, the movement sensor 2 may be integrated in the processing part 5, e.g., in a dedicated apparatus, fixed or fixable to the fixing element 3.

The processing part 5 and the power supply part 6 are arranged herein within a cardiac parameters detection apparatus 10. The cardiac parameters detection apparatus 10 is, for example, formed by a dedicated portable device, an earphone, a smartphone, a smartwatch, a tablet, a portable computer, or other smart apparatus.

The processing part 5 comprises a processing unit 15; one or more memories 16 and an I/O unit 17.

The processing unit 15 may comprise for example a microcontroller, a microprocessor and/or another CPU (Central Processing Unit).

The memory 16 typically comprises a non-volatile memory for programs and data to be stored permanently and one or more buffers for data useful for processing; in particular, in embodiments, it comprises five FIFO memories, indicated as F1-F5 and discussed below. Alternatively, the FIFO memories may be embodied in the processing unit 15. The programs are, for example, executed by the processing unit 15.

The I/O unit 17 comprises units and circuits useful for external communications, for example for sending and/or displaying the cardiac periods S11, S12, S21 and may therefore comprise radio circuits, wireless communication systems, screens, displays, acoustic signalers and the like.

The power supply part 6 comprises herein a battery 20 and a Power Management Integrated Circuit (PMIC) 21, coupled to the processing part 5, and of the known type.

Figure 3:
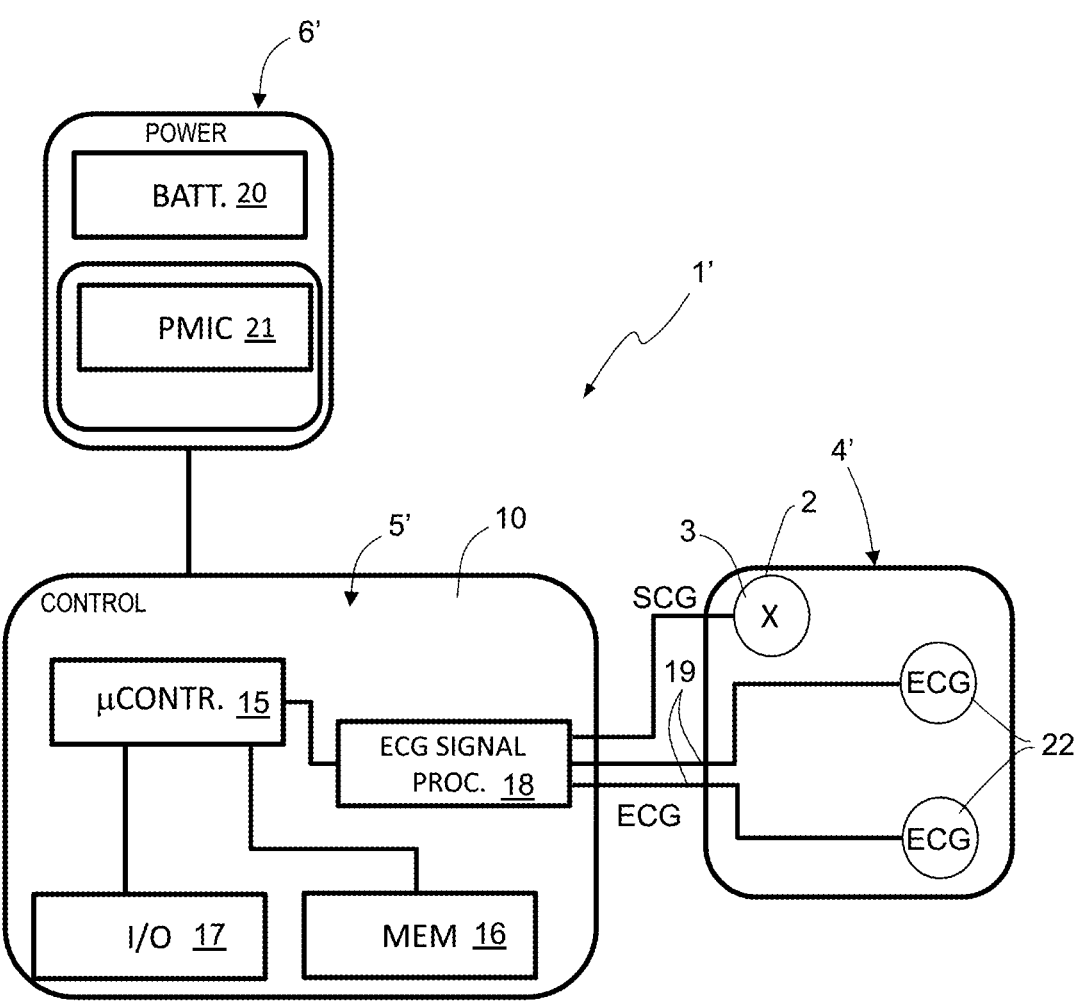
FIG. 3 is a general block diagram of a cardiac parameters measuring system for detecting cardiopathies, according to another embodiment.

FIG. 3 shows a different cardiac parameters detection system, indicated by 1'.

The system 1' has a general structure similar to the system 1 of FIG. 2; therefore like parts are indicated with the same reference numbers.

In the system 1' of FIG. 3, the detection part, indicated by 4', comprises, in addition to the movement sensor 2 and the fixing element 3, two ECG electrodes 20 for detecting the electrocardiographic signal.

The processing part 5' comprises an ECG pre-processing unit 18, for a first processing of the electrocardiographic signal (front-end).

The ECG electrodes 20 and the ECG pre-processing unit 18 may be of the known type and are coupled to each other by cables 19. The ECG pre-processing unit 18 is also connected to the microcontroller 15 to provide the pre-processed signal and allow health predictions to be carried out based on the ECG, as well as SCG plot.

In FIG. 3, furthermore, the power supply part, indicated by 6', is external to the apparatus 10. Alternatively, it might be internal, as in FIG. 2.

The system 1 or 1' of FIG. 2 or 3 is configured to perform a cardiac parameters measuring method, and specifically to extract the systolic and diastolic periods from the signal SCG detected by the movement sensor 2 of FIGS. 2 and 3.

Specifically, the measuring method performed by the systems 1 and 1' is based on:

acquiring a signal SCG through an accelerometer;

processing the signal SCG for obtaining its envelope;

segmenting the sequence for searching the peaks (systolic peak or diastolic peak);

validating the results for identifying systolic peak/diastolic peak pairs; and calculating the parameters, including calculation of the systolic period S12, the diastolic period S21 and, if desired, the cardiac period S11=S12+S21, from the peak pair.

The processing of the signal SCG may comprise a filtering, a possible signal enhancement treatment to amplify the peaks and the calculation of the envelope, for example by calculating the effective value (RMS, Root Mean Square).

The sequence segmentation comprises dividing the signal samples into groups of samples (signal segments) having a repetitive pattern, according to the periodicity of the pattern of the cardiac signal and comprises herein quantizing the signal (transforming the signal into sequences of "0" and "1") and searching for local maxima (peaks) within each sequence wherein the samples have a first logic level (hereinbelow, value "1"), each sequence being delimited by the switching from a second logic level (hereinbelow, value "0") to the first logic level and by the inverse switching from the first logic level to the second logic level.

The validation of the results here comprises identifying pairs of peaks or maxima having characteristics (in the example, amplitude, distance and duration) compatible with the systolic period and the diastolic period.

The calculation of the periods S12, S21 and S11 comprises calculating these periods in each signal segment.

Figure 8:
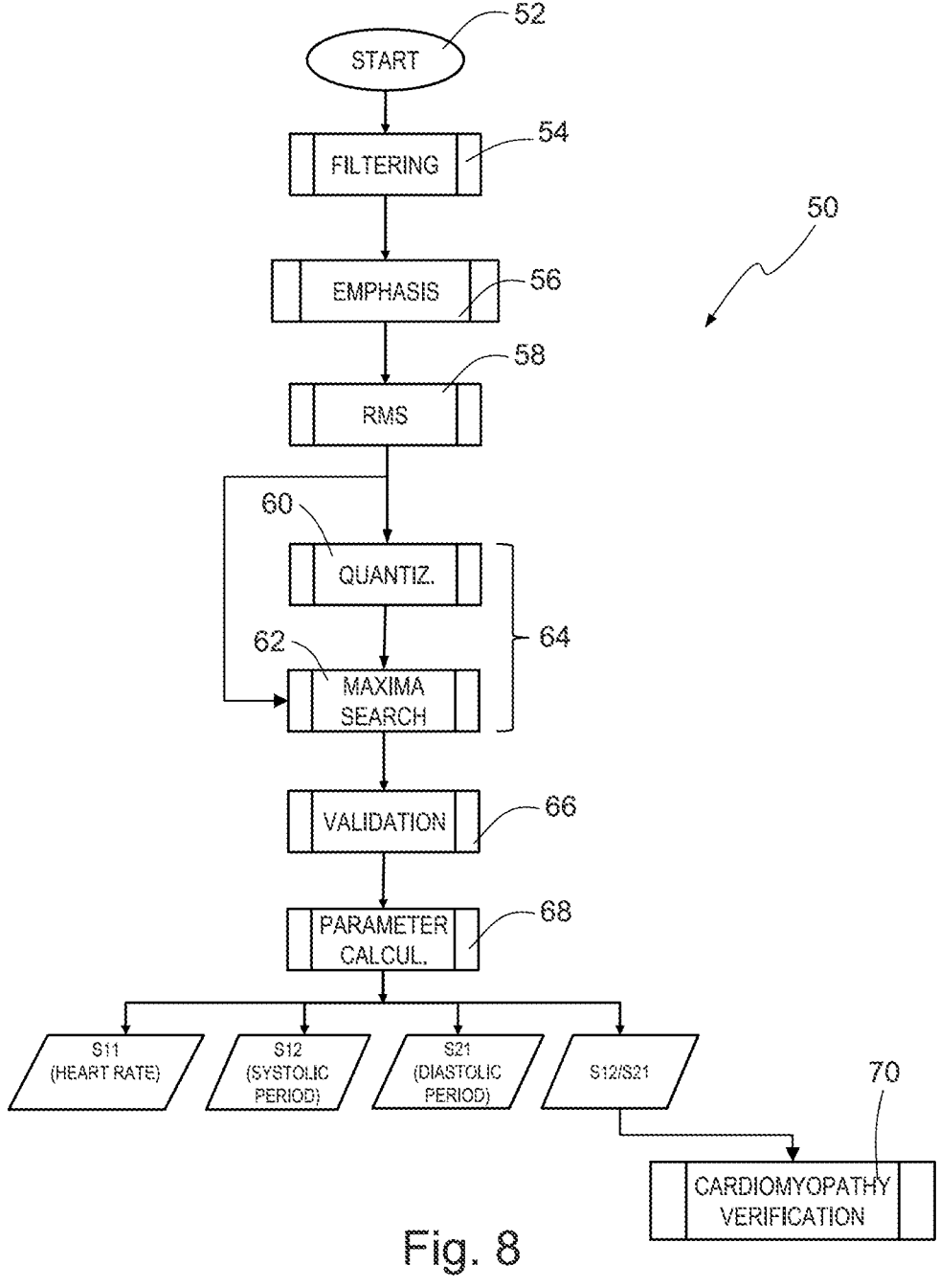
FIG. 8 is a flow diagram relating to the present cardiac signals processing method.

Hereinafter, an embodiment of the present cardiac parameters measuring method will now be described with reference to FIG. 8, showing a principle flow diagram, and to FIGS. 4-7, showing an example of seismocardiographic signal (SCG) detected by the movement sensor 2 and intermediate signals obtainable from the signal SCG, according to the present disclosure.

The cardiac parameters measuring method of FIG. 8, indicated by 50, may be performed by the processing unit 15 of FIG. 2 or 3 and may be activated automatically, for example by the apparatus 10, upon detection of measurement conditions (person at rest, reception of the seismocardiographic signal SCG with characteristics similar to a heartbeat or following activation controlled by the movement sensor 2 using the FSM/MLC (Finite State Machine/Machine Learning Core) resources normally present in commercial accelerometers or manually, through a command, for example provided through the I/O unit 17.

At start-up, step 52, the input signal SCG (seismocardiographic signal) is acquired. The input signal SCG is a digital signal, sampled at a much higher frequency than the cardiac one (for example at about 2 kHz) and highly variable.

The acquired signal may have a variable duration (number of samples), from a minimum value, for example corresponding to two heartbeats. In a manner not shown, after the acquisition of the input signal SCG, a verification may be provided that the duration (number of samples) of the input signal SCG is sufficient for the successive processing, with possible generation of a warning signal and interruption of the cardiac parameters measuring method 50, conversely.

In step 54, the input signal SCG is filtered, to eliminate the unwanted harmonic components of the input signal SCG and high-frequency noise, minimizing the distortion due to the phase shift, i.e., without altering the peaks of the input signal over time, obtaining a filtered signal s1.

Figures 4, 5:
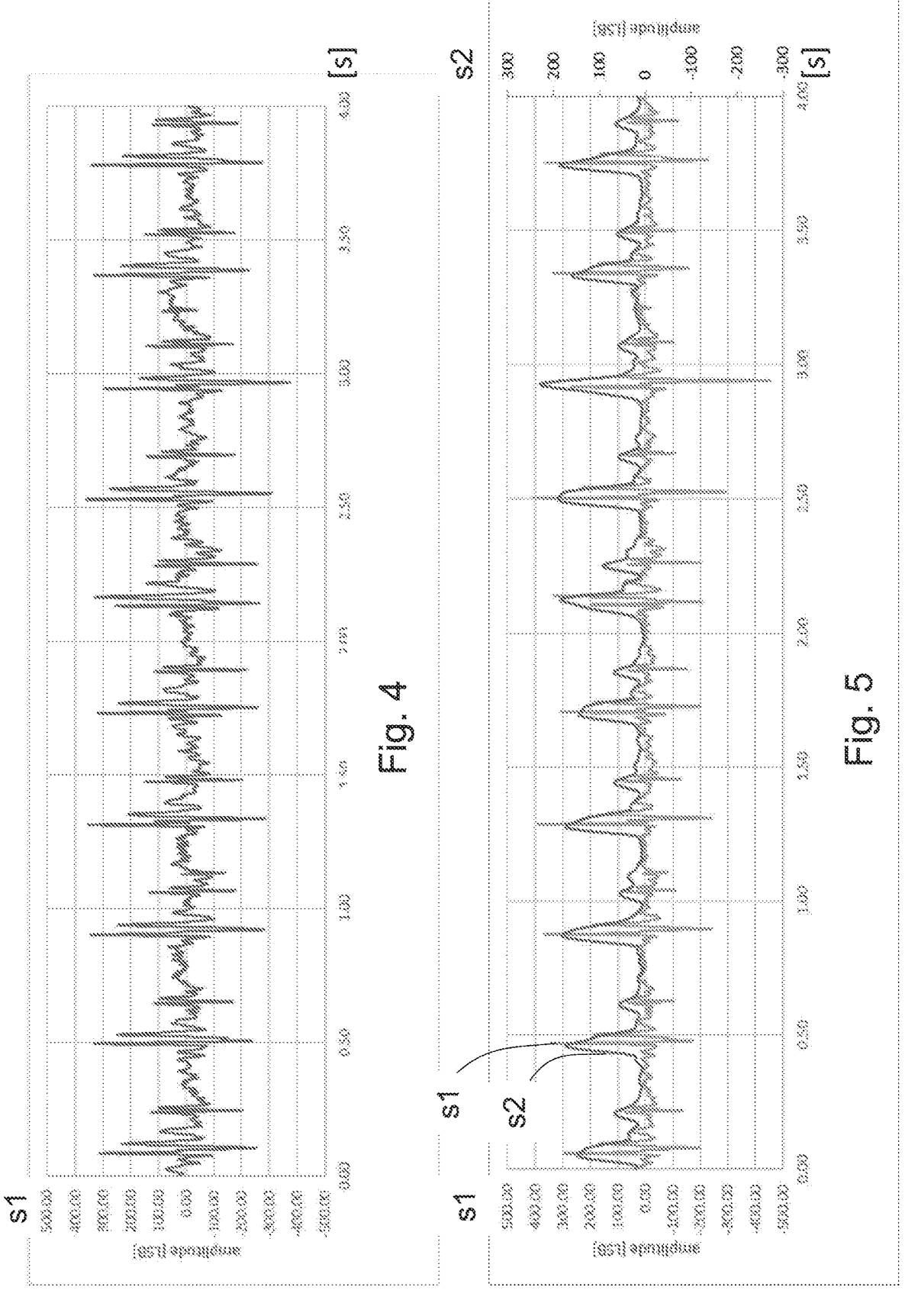
FIGS. 4-7 show examples of signals detected by the system of FIG. 2 or FIG. 3 and of their processing according to the present method.

FIG. 4 shows, for example, a possible pattern of the filtered signal s1.

In step 56, the filtered signal s1 is treated to enhance the characteristics thereof and amplify the amplitude of the peaks with respect to the background noise, using a non-linear function, such as the hyperbolic sine (emphasis phase). In fact, here, the absolute amplitude of the signal is not very relevant; vice versa, the time position of the peaks is of interest.

In step 58 the envelope of the filtered signal s1 is calculated, for example through a calculation operation on a movable window (sliding window) of the root mean square RMS. An envelope signal s2 is thus obtained, shown for example in FIG. 5.

Subsequently, the envelope signal s2 is quantized (i.e., transformed into a sequence of "1" and "0," step 60) and the local maxima thereof are searched (step 62, search for maxima or peaks).

Figures 6, 7:
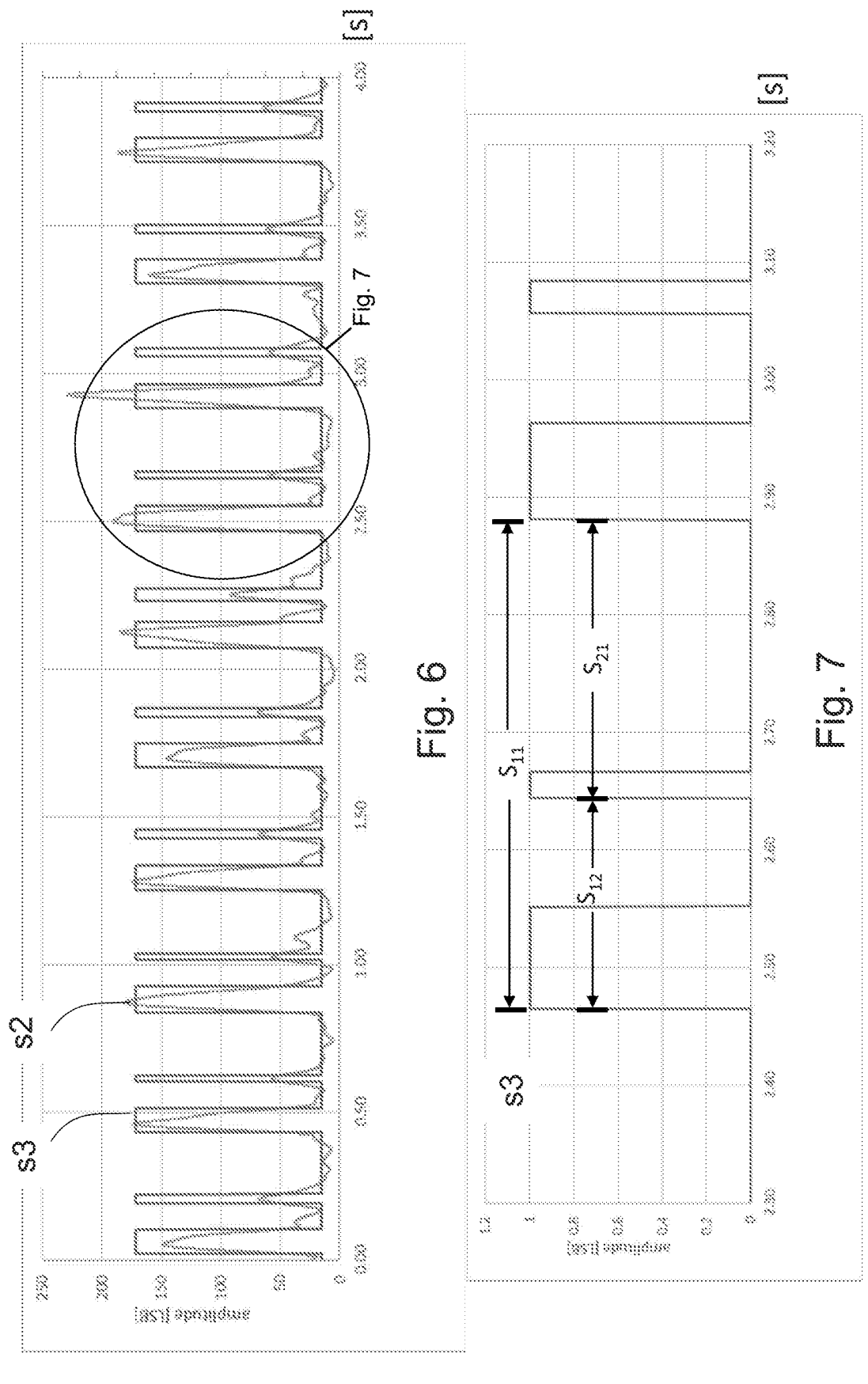

The sequence of "1" and "0" obtained in step 60 is a quantized signal s3, shown in FIG. 6 superimposed on the envelope signal s2.

The set of quantization 60 and maxima search 62 steps is a segmentation step 64. In practice, in step 64, the envelope signal s2 is segmented into groups of repetitive patterns, based on the heartbeat periodicity, and the respective peak is associated with each group (identification and storage of clusters, described in detail below).

In step 66, the data processed in the segmentation step 64 are validated based on some rules for assessing the plausibility thereof and associating pairs of peaks belonging to a same cardiac cycle (period). In fact, knowing the values of the expected periods (normal values and maximum offset in the pathological case) any clearly incorrect measurements and artifacts may be discarded, as explained in detail below, by discarding the implausible peaks/pairs of peaks.

In step 68 the searched characteristics are calculated.

In particular, here the values S12, S21 and S11 are calculated, respectively based on the distance between two successive peaks within a pair of peaks (systolic period S12), the distance between the second peak of a pair of peaks and the first peak of the successive pair of peaks (diastolic period S21) and their sum (i.e., the distance between the first peaks of two successive pairs of peaks, S11, being the heart rate), as shown in the enlarged detail of FIG. 7, and their ratio S12/S21 is calculated. The first peak of each pair of successive peaks is a systolic peak, and the second peak of each pair of successive peaks is a diastolic peak.

Based on these values and in particular on the ratio S12/S21, the system 1 or 1' of FIGS. 2, 3 may highlight a risk of cardiopathy, step 70. In particular, based on the characteristics S12, S21, S11 detected, the value of the following parameters: HFrEF (Heart Failure with reduced Ejection Fraction); HFmrEF (Heart failure with Mid-Range Ejection Fraction); HFpEF (Heart Failure with Preserved Ejection Fraction) may be determined and classified. Furthermore, the detected values may be displayed and/or sent to the outside and warning messages or perfect cardiac functioning messages may be generated.

In this manner, owing to the use of an accelerometer, the ambient noise has no effect on the calculation of the characteristics S12, S21 and S11, which therefore have good reliability.

The systems 1, 1' operate in low-consumption and therefore may be implemented through portable devices; they are also low-cost.

Figure 9:
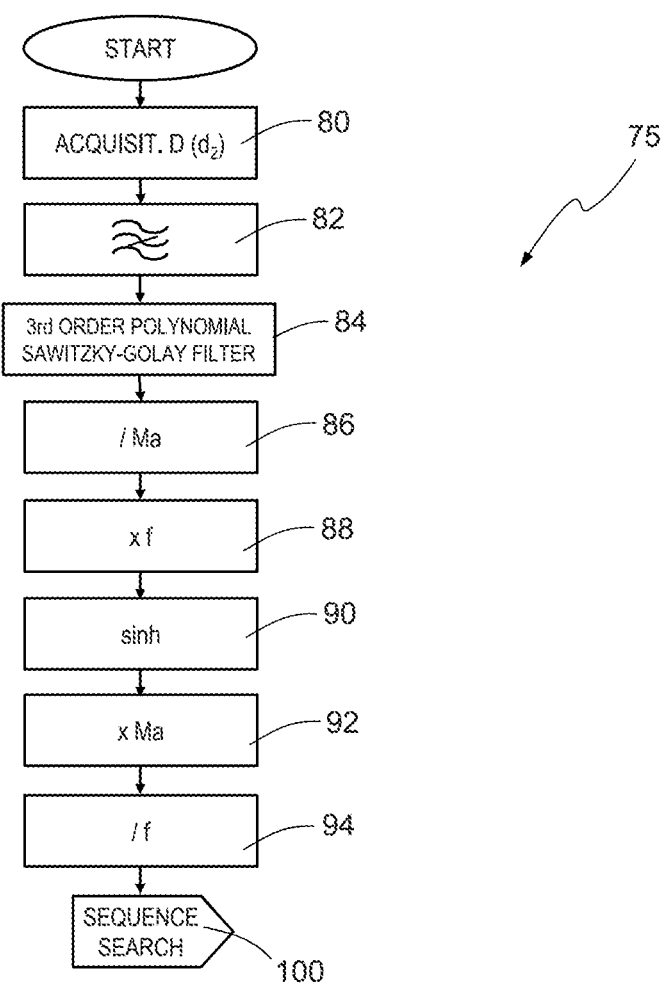
FIGS. 9-11 show in more detail some steps of the method of FIG. 8.
Figure 10:
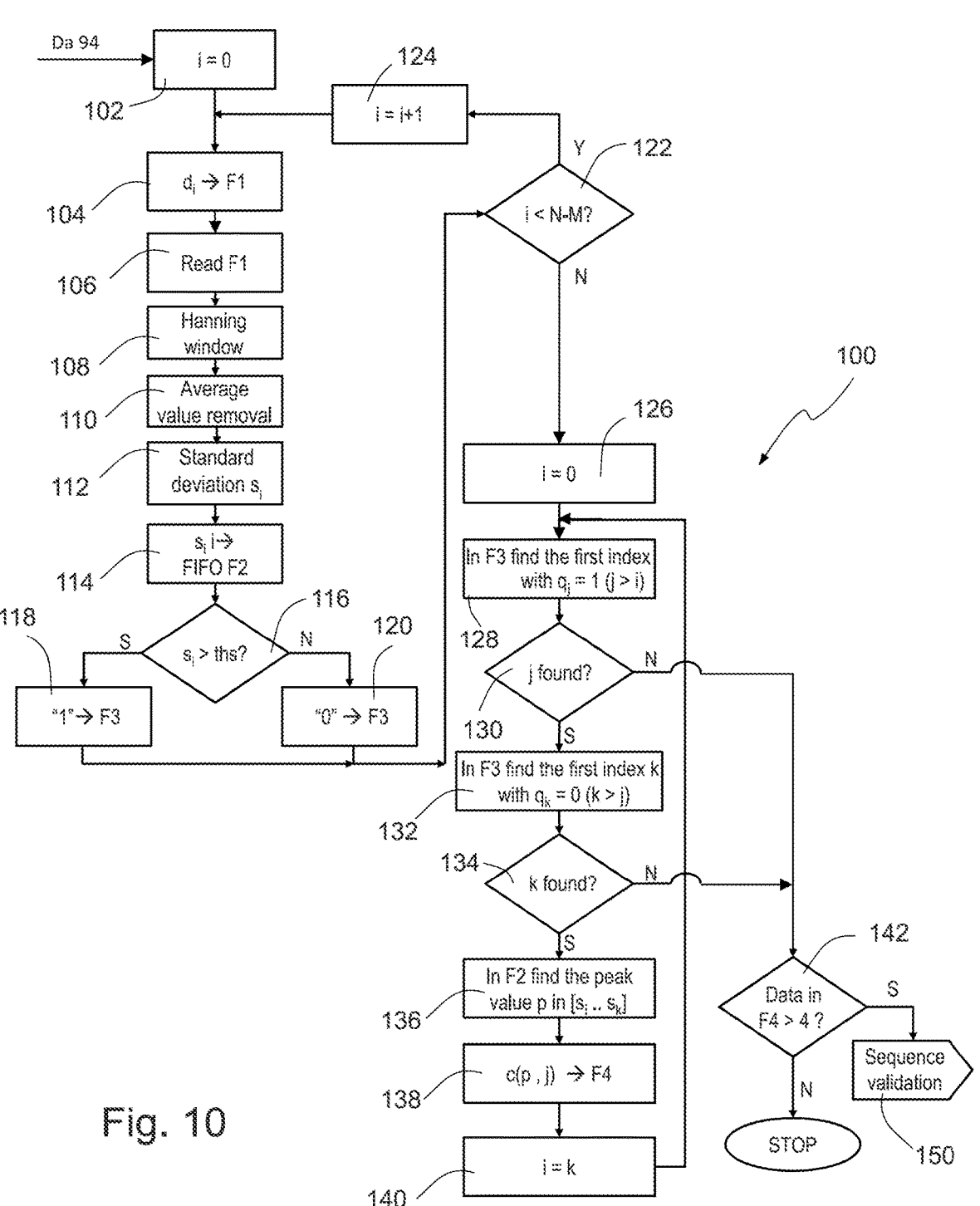
Figure 11:
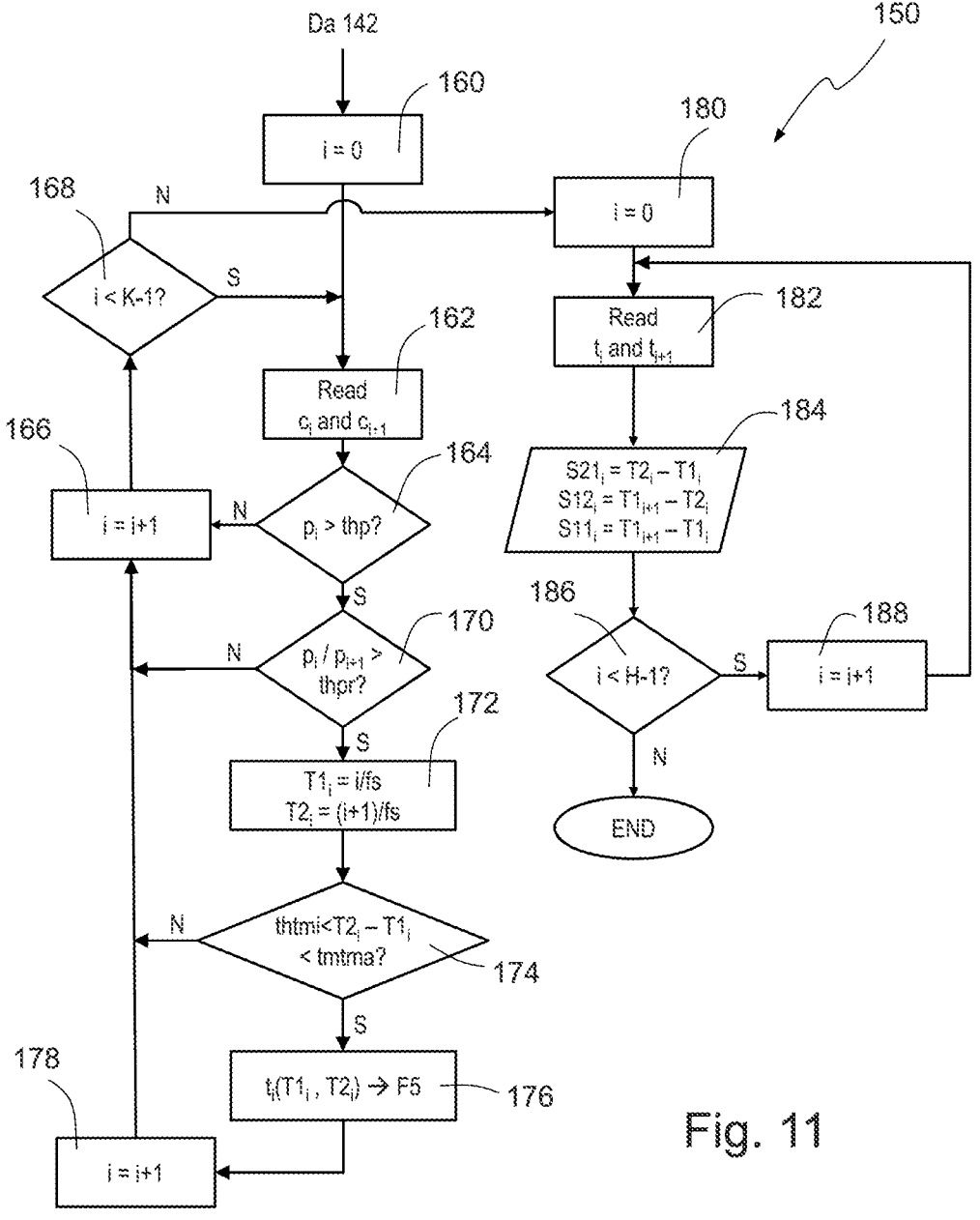

An example of implementation of the cardiac parameters measuring method 50 of FIG. 8 is shown in FIGS. 9-11, described hereinbelow.

FIG. 9 refers to a pre-processing flow of the signal 75, providing an implementation of steps 52-56 of the cardiac parameters measuring method 50 of FIG. 8.

In detail, in step 80, the samples of the input signal SCG are loaded into an array D of input data, for example contained in a memory (not shown) associated with the movement sensor 2 of FIGS. 2 and 3. The array D stores N samples $d_l$.

In step 82, the samples $d_l$ are filtered, in particular in a band-pass filter having a bandwidth correlated to the heart rhythm (for example comprised between 1 Hz and 150 Hz); in step 84, the filtered samples $d_l$ are subject to a further filtering to reduce small local oscillations, for example by using a third-order polynomial Sawitzky-Golay filter. Steps 82, 84 implement, for example, step 54 of FIG. 8.

In step 84, the amplitude of the filtered samples $d_l$ in step 82 is divided by Ma (theoretical maximum value; in step 86 they are multiplied by an expansion factor f, thus carrying out a normalization of the samples. Then, in step 88, the normalized samples $d_l$ are amplified, using for example a hyperbolic sine function. In this manner, there is a greater amplification of the signal peaks with respect to the lower values, subsequently facilitating the search for local maxima.

Note that the theoretical maximum value Ma and the expansion factor f are generally variable with the system 1, 1', with the patient's physiology and with the degree of mechanical coupling of the movement sensor 2 to the patient. However, they are not critical values and may be preset and possibly modified in a successive calibration step, following a command from an advanced user or after the system 1, 1' has confirmed the correctness/plausibility of the acquired signal.

Then, step 92, the samples $d_l$ that are amplified are multiplied by the theoretical maximum value Ma and, in step 94, are divided by the expansion factor f, constituting processed signals, again indicated, for the sake of clarity, by $d_l$.

In practice, the set of steps 86-94 implements step 56 of enhancing the signal of FIG. 8.

Steps 86-94 of enhancing the signal are performed on all samples of the input signal SCG.

The method then proceeds with the sequence search flow 100, described hereinbelow with reference to FIG. 10.

The sequence search flow 100 implements the envelope calculation 58 and segmentation 64 (including quantization 60 and local maxima search 62) steps.

In particular, the envelope calculation step 58 is performed based on a sliding window, that is, at the beginning, the sequence search flow 100 receives a processed sample $d_l$ resulting from step 94 and this is processed together with the preceding M−1 normalized samples, as described hereinbelow.

In detail, in step 102, a counter i is initialized, for example to zero.

In step 104, the processed sample $d_l$ just received is loaded into a samples buffer, for example into the memory F1 of FIG. 2, hereinafter referred to as processed samples memory F1. The processed samples memory F1 has M memory locations, equal to the number of samples of the sliding window.

In step 106, after a verification that the processed samples memory F1 has stored M samples (corresponding to a sliding window), all the processed samples $d_l$ present in the normalized samples memory F1 (belonging to a same sliding window) are read; in step 108, they are subject to a Hanning window function; then, in step 110, they are subject to an average value removal operation; and, in step 112, they are subject to a standard deviation calculation operation (RMS calculation), which provides a standard deviation value $s_i$.

Steps 108, 110 and 112 allow calculating the envelope of the processed signal s1, formed by the plurality of standard deviation values $s_i$ and constituting the envelope signal s2, shown for example in FIG. 5, and implementing the envelope calculation step 58.

In step 114, the standard deviation value $s_j$ just calculated is loaded into a suitable standard deviation buffer, for example in the memory F2 of FIG. 2, also referred to as the standard deviation memory F2. The standard deviation memory F2 has N-M memory locations, due to the first samples loaded to have a sufficient number for the processings of an observation window (sliding window).

In step 116, the standard deviation value $s_j$ just calculated and stored is compared with a deviation threshold ths. The deviation threshold ths depends on the signal detected and may be set in a calibration step of the system 1, 1' of FIGS. 2 and 3 in a preliminary step of the cardiac parameters measuring method 50.

In the event that the standard deviation value $s_i$ just calculated and stored is higher than the deviation threshold ths (output YES from step 116), a logic "1" is stored in a quantized values buffer, for example in the memory F3 of FIG. 2, step 118; in the event that the standard deviation value $s_i$ is lower than or equal to this threshold ths (output NO from step 116), a logic "0" is stored in the quantized values memory F3, step 120.

The quantized values memory F3 has N-M memory locations.

Steps 116, 118 and 120 therefore allow a quantization of the amplitude to be performed (corresponding to step 60 of FIG. 8).

Then, step 122, it is verified whether the condition i<N−M applies, that is, whether all the N samples of the processed signal $d_l$ loaded in the array D have not yet been processed, except for the last M−1 samples (in a number that is insufficient to define a sample assessment window).

In the positive case, output YES from step 122, in step 124 the counter i is increased and the method returns to step 104, loading a successive normalized sample $d_l$.

In the negative case, output NO from step 122, the method goes to a signal maxima search step, corresponding to step 62 of FIG. 8.

In practice, at the end of the loop defined by steps 104-124, the quantized values memory F3 (FIG. 2) contains a sequence of N−M digital values $q_i$ of value 0 or 1, wherein the zeros (corresponding to low standard deviation values) have sequences of 1 therebetween, usually shorter, corresponding to time intervals in which the envelope signal s2 is significant (except for spurious values which are eliminated in the successive processing), as shown in FIG. 6.

In the maxima search step, initially, step 126, the counter i is initialized again, for example to zero.

In step 128, the first quantized value $q_j$ (with j>i) which is equal to "1" is searched in the quantized values memory F3. Here, j represents in practice the position (time) in which the quantized signal s3 (FIGS. 6, 7) has a rising edge.

If the value j which meets the condition of step 128 is found, output YES from step 130, the first quantized value $q_k$ (with k>j), which is equal to "0," is searched in the same quantized values memory F3, step 132. In practice, here, k represents the position (time) in which the quantized signal s3 has a falling edge successive to the rising edge found previously.

If the value that meets the condition of step 132 is found, output YES from step 134, the peak is searched between the standard deviation values $s_j$ (envelope signal s2) stored in the standard deviation memory F2 and comprised in the interval between the indices j and k, and the peak amplitude p thereof is acquired, step 136.

In step 138, the cluster formed by the peak amplitude p and by the time in which the peak (identified by its index j within the standard deviation buffer F2) begins is stored within a time memory, for example in the memory F4 of FIG. 2, hereinafter also referred to as cluster memory F4. The cluster is indicated by c(p, j) in FIG. 10 and the cluster memory F4 comprises K memory locations, with K<M−N.

In step 140, the index i is set equal to k and the sequence search flow 100 returns to step 128, for searching a new cluster c(p, j).

Steps 116-140 therefore allow a segmentation of the sequence of standard deviation values to be performed (corresponding to step 64 of FIG. 8).

In the event that a value is not found that meets the condition of step 128 (output No from step 130) or step 132 (output NO from step 134), i.e., a rising edge or a falling edge is not detected in the remaining part of the quantized signal s3 of FIG. 6, the method proceeds to step 142, where it is verified whether the cluster memory F4 contains a minimum number of peaks (here equal to 4).

In the negative case, output NO from step 142, the sequence search flow 100 stops, possibly sending an error message; in the positive case, output YES from step 142, the method proceeds with the parameters validation/calculation flow 150, described hereinbelow with reference to FIG. 11.

The parameters validation/calculation flow 150 of FIG. 11 implements the parameters validation 66 and calculation 68 steps of FIG. 8. In practice, during the validation, it is verified that the clusters $c_i$ meet certain plausibility factors and for these the method proceeds with the calculation of the parameters.

In particular, in the parameters validation/calculation flow 150 of FIG. 11, to eliminate spurious peaks and to eliminate, for example, the segments in which a peak is "lost," verifications of peak amplitude, correct systolic peak/diastolic peak sequence and correct distance between peaks are performed.

In detail, in the parameters validation/calculation flow 150 it is verified that the peaks have a minimum amplitude, that the ratio of the amplitudes between two successive peaks is greater than a predetermined peak threshold (i.e., that a diastolic peak follows a systolic peak), and that the distance between two successive peaks is comprised in an admissibility window.

Specifically, in step 160 of FIG. 11, the index i is initialized again, for example to zero.

In step 162, the i-th cluster ($c_i$) and the successive one ($c_{i+1}$), pair of successive clusters, are read.

In step 164, it is verified whether the peak amplitude $p_i$ in the cluster $c_i$ (first peak of the pair of successive clusters) exceeds a predetermined amplitude threshold thp, for example set in a calibration step.

In the negative case, output NO from step 164, the counter i is increased, step 166, and it is verified whether the increased value of the counter i is lower than K−1 (i.e., whether further clusters are present in the cluster memory F4), step 168.

If the verification in step 168 gives a positive outcome (output YES), the parameters validation/calculation flow 150 returns to step 162 to analyze two other successive peaks, typically the second peak of the previous verification and the peak following the same.

If the verification in step 164 gives a positive outcome (output YES), it is verified whether the amplitude ratio between the peak amplitude $p_i$ and the successive peak amplitude $p_{i+1}$ is higher than a peak ratio threshold thpf, step 170.

In the negative case, output NO from step 170, two other successive peaks are verified, returning to step 166; in the positive case (indicative of the fact that the peak $p_i$ is due to the systolic period and the successive peak $p_{i+1}$ is due to the diastolic period of a same cardiac cycle), it is verified that they are placed at an acceptable time distance. For this purpose, in step 172 the times $T1_i$ and $T2_i$ are determined (referred to the i-th peak and, respectively, to the successive i+1-th peak) by dividing the indices i and i+1 by the sampling frequency fs of the input signal SCG.

In step 174 it is verified whether the distance between the two peaks (i and i+1) is comprised between a lower distance threshold Thtmi and a higher distance threshold Thtma.

In the negative case, output NO from step 174, a successive peak is verified, returning to step 166; in the positive case, output YES, the time pair $T1_i$, $T2_i$ (indicated as pair $t(T1_i, T2_i)$ in FIG. 11) is stored in a buffer, for example in the memory F5 of FIG. 2, hereinafter referred to as peak time memory F5. The peak time memory F5 has H memory locations.

Then, step 178, the counter i is increased by one unit and the parameters validation/calculation flow 150 returns to step 166, further increasing the counter i, to search a successive pair of peaks $p_i$ and $p_{i+1}$.

In practice, steps 160-178 of FIG. 11 implement the sequence validation step 66 of FIG. 8.

If the verification in step 168 gives a negative outcome (output NO), i.e., if further pairs of peaks $p_i$, $p_{i+1}$ are not present in the cluster memory F4, the parameters validation/calculation flow 150 proceeds to step 180, where the counter i is initialized again, resetting the same.

In step 182, the i-th time pair, $t(T1_i, T2_i)$, is read from the peak time memory F5.

Then, in step 184, the parameters S12, S21 and S11 are calculated for the i-th pair, for example as:

$$S12_i = T2_i - T1_i$$

$$S21_i = T1_{i+1} - T2_i$$

$$S11_i = T1_{i+1} - T1_i$$

and the parameters just calculated are provided for their further processing and/or display, as indicated in the verification step 70 of FIG. 8.

In step 186 it is verified whether all the time pairs $t(T1_i, T2_i)$ present in the peak time memory F5 have been considered, by verifying whether the counter i has reached the last element of the peak time memory F5; in the negative case, output YES from step 186, the index i is increased, step 188 and the parameters validation/calculation flow 150 returns to step 182 for reading a successive time pair.

If all the elements of the peak time memory F5 have been considered, output NO from step 186, the parameters validation/calculation flow 150 stops.

As an alternative to what has been described above, the calculated parameters may be provided for their display/processing simultaneously at the end of the parameters validation/calculation flow 150.

In the event that the cardiac parameters measuring method 50 is performed by the system 1' of FIG. 3, at the end of the parameters validation/calculation flow 150 it may comprise steps for acquiring the electrocardiographic signal from the EI electrodes 20, for further processings.

The system and the method described herein have numerous advantages.

In particular, they allow the systolic, diastolic and cardiac periods to be reliably measured, owing to the fact that the accelerometer is not very subject to external noises and is capable of rejecting the noise due to breathing. In fact, this is at very different frequencies from the heartbeat and may be eliminated by the initial filtering step and therefore does not affect the measurement.

The measuring system 1, 1' is compact and may therefore be implemented in a portable device or apparatus.

Furthermore, since the accelerometer is already present in many wearable and portable devices, the system and method described allow a cardiac functioning analysis function to be added to the current devices already present on the market at a very low cost.

The method has proven to be reliable and effective and may provide an early warning for performing further, more in-depth medical analysis.

Finally, it is clear that modifications and variations may be made to the system and method described and illustrated herein without thereby departing from the scope of the present disclosure.

For example, taking into account the fact that the most recent generations accelerometers are often provided with algorithms for detecting activities (resting, walking, running . . . ), embedded in the system and capable of performing in parallel the steps of the present method, they may integrate the hardware and software blocks/modules (however coded) for implementing the method.

Furthermore, taking into account the ability, in recent accelerometers, to detect the patient's status (lying or standing), this detection may be used to activate/suspend the measurement.

In the previous description, the processing and analysis of the signals are carried out in "discontinuous" mode, i.e., based on a pre-acquired signal.

In this operating mode, the processing unit 15 works on two processes: a first process acquires data when possible (stationary person) or following a trigger (as explained above) and records it in the array D for X seconds, for example for 8 seconds; subsequently, a second process analyzes the data of the previous X seconds and calculates the parameters sought in a considerably shorter time, for example 100 ms (depending on the calculation capacity of the processing unit 15); at the end, the second process may analyze a successive group of data present in the array D.

This mode involves a compromise in choosing times: if a short acquisition time is chosen, it is possible to have fast responses, but the analysis risks being fragmented (the beats at the end of one sequence and those at the beginning of the successive one are not correlatable, adjacent beats are used to perform sequence control); if instead a long acquisition time is chosen, it is possible to have a continuous analysis and a better control of the invalid values/clusters, but it has a delayed response time.

Alternatively, the flow described may be modified in a simple manner so as to operate "online," without discontinuity or fragmentation on the data flow.

According to the present disclosure, according to a first example, a system for measuring cardiac parameters, comprises:
a movements sensor (2), configured to generate a seismocardiographic signal (SCG);

a cardiac parameters calculation unit (15), receiving the seismocardiographic signal and including:
envelope determination means (58), configured to generate an envelope signal (s2) correlated to the seismocardiographic signal;
segmentation means (64) configured to identify, in the envelope signal, signal segments having a repetitive pattern;
validation means (150) configured to identify, among the signal segments, pairs of successive peaks such that a first peak of each pair of successive peaks is a systolic peak and a second peak of each pair of successive peaks is a diastolic peak; and
parameters calculation means (68, 70), configured to calculate a systolic period (S12) and a diastolic period (S21) for each pair of successive peaks.

The system according to example 1 may further comprise a filtering module (54), including a band-pass filter (82), coupled to the movements sensor (2) and to the envelope determination means (58) and configured to filter the seismocardiographic signal (SCG) and generate a filtered signal (s1).

In the system according to example 1 or 2, the envelope determination means (58) may comprise calculation means (86-94) configured to calculate a plurality of standard deviation values ($s_j$).

In the system according to any of the preceding examples, the segmentation means (64) may comprise a quantization module (60; 116-120), configured to generate a sequence of quantized samples (s3) having a first logic level when the envelope signal (s2) exceeds a threshold and a second logic level when the envelope signal (s2) is lower than the threshold.

In the system according to the preceding example, the segmentation means (64) may further comprise a maxima search module (62; 128, 132, 136) configured to search, within the sequence of quantized samples (s3), maximum values of the envelope signal (s2) between a switching time of the quantized samples between the first and the second logic levels and a successive switching time, and a cluster generation module (138), configured to associate the switching times with respective maximum values of the envelope signal (s2) forming clusters.

In the system according to the preceding example, the maxima search module (62; 128, 132, 136) may be configured to search, within the sequence of quantized samples (s3), a start-of-peak timing, wherein a quantized sample of the sequence of quantized samples (s3) switches from the first to the second logic level, and an end-of-peak timing, successive to the start-of-peak timing, wherein a quantized sample of the sequence of quantized samples (s3) switches from the second to the first logic level, and the maxima search module may further comprise a maximum amplitude search module (136), configured to search, in the envelope signal (s2), between the start-of-peak timing and the end-of-peak timing, a local maximum value (p), and wherein the cluster generation module (138) is configured to associate the start-of-peak timing with the maximum value of the envelope signal (s2).

In the system according to any of the preceding examples, the validation means (150) may comprise a peak validation module (164), configured to verify that the values of the envelope signal (s3) of the clusters exceed a threshold and a characteristics comparison module (170, 174), configured to verify that characteristics ($p_i$, $T_i$; $T_{i1}$, $T_{i2}$) of the envelope signal (s3) of successive clusters meet a predetermined relationship.

In the system according to the preceding example, the successive peak pairs comparison module (164, 70, 172) may comprise at least one of:

an amplitude verification module, configured to verify that a first peak of the pair of successive peaks has an amplitude greater than an amplitude threshold;

an amplitude ratio verification module, configured to verify that a first peak of the pair of successive peaks and a second peak of the pair of successive peaks have an amplitude ratio satisfying a ratio relationship; and a peak distance verification module, configured to verify that a distance between a first peak of the pair of successive peaks and a second peak of the pair of successive peaks meets a distance relationship.

In the system according to any of the preceding examples, the parameters calculation means (68) may comprise a cardiac period determination module (S11) and a ratio determination module (70), configured to calculate a ratio (S12/S21) between the systolic period (S12) and the diastolic period (S21) of each pair of successive peaks.

In the system according to the preceding example, the duration determination module (184) may be further configured to calculate the duration of a cardiac cycle from the duration of the systolic peak and the duration of the diastolic peak in each pair of successive peaks.

In the system according to any of the preceding examples, the movements sensor may comprise an accelerometer (2).

According to another example, a method for measuring cardiac parameters, comprises:

generating a seismocardiographic signal;

generating an envelope signal correlated to the seismocardiographic signal;

segmenting the envelope signal into signal segments having a repetitive pattern;

identifying, among the signal segments, pairs of successive peaks such that a first peak of each pair of successive peaks is a systolic peak and a second peak of each pair of successive peaks is a diastolic peak; and calculating a systolic period and a diastolic period for each pair of successive peaks.

The method according to the preceding example may further comprise filtering the seismocardiographic signal with a band-pass filter and generating a filtered signal, wherein generating an envelope signal comprises calculating an envelope of the filtered signal.

In the method according to the preceding example, generating an envelope signal may comprise calculating a plurality of standard deviation values ($s_j$).

Furthermore, segmenting the envelope signal may comprise generating a sequence of quantized samples having a first logic level when the envelope signal exceeds a threshold and a second logic level when the envelope signal is lower than the threshold.

In the method according to the preceding example, segmenting the envelope signal may comprise searching, within the sequence of quantized samples (s3), maximum values of the envelope signal (s2) between a switching time of the quantized samples between the second and the first logic levels and a successive switching time from the first to the second logic level, and associating the switching times with respective maximum values of the envelope signal (s2) forming clusters.

In the method according to any of the preceding examples, identifying, among the signal segments, pairs of successive peaks may comprise verifying that the values of the envelope signal (s3) of the clusters exceed a threshold and verifying that characteristics ($p_i$, $T_i$; $T_{i1}$, $T_{i2}$) of the envelope signal (s3) of successive clusters meet a predetermined relationship.

The method according to the preceding example may further comprise calculating a cardiac period (S11) and calculating a ratio (S12/S21) between the systolic period (S12) and the diastolic period (S21) of each pair of successive peaks.

The method according to the preceding example may further comprise calculating a ratio between the duration of the systolic peak and the duration of the diastolic peak and generating cardiac health information based on the ratio.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for measuring cardiac parameters, the system comprising:

a movements sensor configured to generate a seismocardiographic signal; and a processor configured to:

receive the seismocardiographic signal;

generate an envelope signal correlated to the seismocardiographic signal;

identify, in the envelope signal, signal segments having a repetitive pattern, the processor, in the identification of the signal segments, generates a sequence of quantized samples having a first logic level in a case where the envelope signal exceeds a threshold and a second logic level in a case where the envelope signal is lower than the threshold, searches, within the sequence of quantized samples, maximum values of the envelope signal between a switching time of the quantized samples between the first and the second logic levels and a successive switching time, and associates the switching time and the successive switching time with respective maximum values of the envelope signal forming clusters;

identify, among the signal segments, pairs of successive peaks such that a first peak of each pair of successive peaks is a systolic peak and a second peak of each pair of successive peaks is a diastolic peak; and calculate a systolic period and a diastolic period for each pair of successive peaks.

2. The system according to claim 1, further comprising:

a band-pass filter configured to filter the seismocardiographic signal and generate a filtered signal.

3. The system according to claim 1, wherein the processor is configured to calculate a plurality of standard deviation values.

4. The system according to claim 1, wherein the processor is configured to:

search, within the sequence of quantized samples, a start-of-peak timing in which a quantized sample of the sequence of quantized samples switches from the first to the second logic level, and an end-of-peak timing successive to the start-of-peak timing and in which a quantized sample of the sequence of quantized samples switches from the second logic level to the first logic level;

search, in the envelope signal, between the start-of-peak timing and the end-of-peak timing, a local maximum value; and associate the start-of-peak timing with the local maximum value of the envelope signal.

5. The system according to claim 1, wherein the processor is configured to:

verify that values of the envelope signal of the clusters exceed a threshold; and verify that characteristics of the envelope signal of successive clusters meet a predetermined relationship.

6. The system according to claim 1, wherein the processor is configured to calculate a cardiac period, and calculate a ratio between the systolic period and the diastolic period of each pair of successive peaks.

7. The system according to claim 1, wherein the movements sensor includes an accelerometer.

8. A method for measuring cardiac parameters, comprising:

generating a seismocardiographic signal;

generating an envelope signal correlated to the seismocardiographic signal;

segmenting the envelope signal into signal segments having a repetitive pattern, the segmenting of the envelope signal includes generating a sequence of quantized samples having a first logic level in a case where the envelope signal exceeds a threshold and a second logic level in a case where the envelope signal is lower than the threshold, searching, within the sequence of quantized samples, maximum values of the envelope signal between a switching time of the quantized samples between the second and the first logic levels and a successive switching time from the first to the second logic level, and associating the switching time and the successive switching time with respective maximum values of the envelope signal forming clusters;

identifying, among the signal segments, pairs of successive peaks such that a first peak of each pair of successive peaks is a systolic peak and a second peak of each pair of successive peaks is a diastolic peak; and calculating a systolic period and a diastolic period for each pair of successive peaks.

9. The method according to claim 8, further comprising filtering the seismocardiographic signal with a band-pass filter and generating a filtered signal, wherein generating the envelope signal includes calculating an envelope of the filtered signal.

10. The method according to claim 8, wherein identifying, among the signal segments, pairs of successive peaks includes verifying that values of the envelope signal of the clusters exceed a threshold, and verifying that characteristics of the envelope signal of successive clusters meet a predetermined relationship.

11. The method according to claim 10, further comprising calculating a cardiac period, and calculating a ratio between the systolic period and the diastolic period of each pair of successive peaks.

12. A device, comprising:

a sensor configured to generate a seismocardiographic signal; and a processor configured to:

generate an envelope signal of the seismocardiographic signal;

segment the envelope signal into signal segments having a repetitive pattern, the processor, in the segmentation of the envelope signal, generates a sequence of quantized samples having a first logic level in a case where the envelope signal exceeds a threshold and a second logic level in a case where the envelope signal is lower than the threshold;

determine pairs of successive peaks in the signal segments, respectively, each of the pairs of successive peaks including a first peak having the first logic level and a subsequent second peak having the first logic level; and determine a plurality of characteristics including a heart rate, a systolic period, and a diastolic period based on the pairs of successive peaks, the processor, in the determination of the plurality of characteristics, determines the systolic period based on a first time length between the first peak and the second peak in a first pair of the pairs of successive peaks;

determines the diastolic period based on a second time length between the second peak in the first pair of the pairs of successive peaks and the first peak of a second pair of the pairs of successive peaks; and determines the heart rate based on a sum of the first time length and the second time length.

13. The device according to claim 12, wherein the first peak is a systolic peak and the second peak is a diastolic peak.

* * * * *